United States Patent [19]

Mrozik

[11] Patent Number: 4,550,160

[45] Date of Patent: Oct. 29, 1985

[54] PROCESSES FOR THE INTERCONVERSION OF C-076 COMPOUNDS

[75] Inventor: Helmut H. Mrozik, Matawan, N.J.

[73] Assignee: Merck & Co., Inc., Rahway, N.J.

[21] Appl. No.: 66,255

[22] Filed: Aug. 13, 1979

[51] Int. Cl.$^4$ ............................................. C07H 17/08
[52] U.S. Cl. ..................................................... 536/7.1
[58] Field of Search .............................. 536/17 R, 10; 204/158 R

[56] References Cited

U.S. PATENT DOCUMENTS

| | | | |
|---|---|---|---|
| 4,053,591 | 10/1977 | Daniels et al. | 536/17 |
| 4,078,139 | 3/1978 | Barton et al. | 536/10 |

FOREIGN PATENT DOCUMENTS

| | | | |
|---|---|---|---|
| 0001689 | 5/1979 | European Pat. Off. | 536/17 |
| 2717040 | 11/1977 | Fed. Rep. of Germany | 536/17 |

OTHER PUBLICATIONS

Whitmore, *Organic Chemistry*, (New York, Cover Publications, Inc., 1951), 2nd ed., p. 456.

Hilgetag et al., (Hilgetag), Monatsberg. Deut. Akad. Wiss., Berlin, 6, 585–593 (1964), *Chem. Abst.*, 62:5165h, (1965).

Al-Kazimi et al., (Al-Kazimi), "A Study of the Schonberg Rearrangement of Diaryl Thiolcarbonates," *J. Am. Chem. Soc.*, 77, 2479–2482, (1955).

Wagner et al., Synthetic Organic Chem., John Wiley & Sons Inc., 1953.

*Primary Examiner*—Jane T. Fan
*Attorney, Agent, or Firm*—David L. Rose

[57] ABSTRACT

The C-076 compounds are a series of four pairs of macrolides in which the members of each pair are homologous. The instant processes convert the C-076 A2 and B2 compounds isolated from a fermentation broth into the biologically preferred B1 and A1 compounds or into the dihydro derivatives thereof.

6 Claims, No Drawings

PROCESSES FOR THE INTERCONVERSION OF C-076 COMPOUNDS

BACKGROUND OF THE INVENTION

The C-076 compounds are a series of compounds which are isolated from the fermentation broth of *Streptomyces avermitilis*. The morphological characteristics of the culture, as well as the fermentation methods and process of isolation of the C-076 compounds is described in the West German published patent Application Ser. No. 27,170,407. Based on taxonomic studies, the microorganisms capable of producing these C-076 compounds are of a new species of the genus Streptomyces, which has been named *Streptomyces avermitilis*. One such culture, isolated from soil is designated MA-4680 in the culture collection of Merck & Co., Inc., Rahway, N.J. A C-076 producing sample of this culture has been deposited in the permanent culture collection of the Fermentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

C-076 producing mutants of *Streptomyces avermitilis* may be obtained by natural selection or those produced by mutating agents including X-ray irradiation, ultraviolet irradation, nitrogen mustard or like treatments, and such are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

The compounds having the following structure:

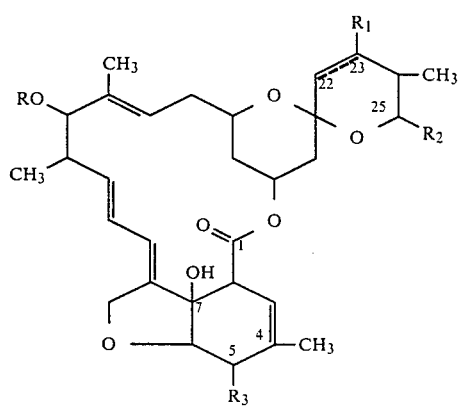

wherein R is the 4'-(α-L-oleandrosyl)-α-L-oleandrose group of the structure:

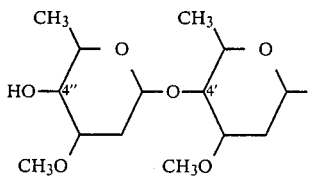

and wherein the broken line indicates a single or double bond;

$R_1$ is hydroxy and is present only when said broken line indicates a single bond;

$R_2$ is iso-propyl or sec-butyl; and $R_3$ is methoxy or hydroxy.

There are eight different C-076 compounds and they are given the designations A1a, A1b, A2a, A2b, B1a, B1b, B2a, B2b, based upon the structure of the individual compounds.

With reference to the $R_1$, $R_2$ and $R_3$ groups of the above structural formula, the individual C-076 compounds are set forth below:

|     | $R_1$       | $R_2$     | $R_3$   |
|-----|-------------|-----------|---------|
| A1a | Double Bond | sec-butyl | —OCH₃   |
| A1b | Double Bond | iso-propyl| —OCH₃   |
| A2a | —OH         | sec-butyl | —OCH₃   |
| A2b | —OH         | iso-propyl| —OCH₃   |
| B1a | Double Bond | sec-butyl | —OH     |
| B1b | Double Bond | iso-propyl| —OH     |
| B2a | —OH         | sec-butyl | —OH     |
| B2b | —OH         | iso-propyl| —OH     |

The C-076 compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition, derivatives of the C-076 compounds have been prepared. In particular, the 22,23-dihydro derivatives of the 1-series of compounds have been found to have particularly advanageous biological properties. The 22,23-dihydro derivatives are prepared by selectively hydrogenating the 22,23 unsaturated prescursor. That is such compounds are prepared from the C-076 A1/A1b and C-076 B1a/B1b pair of compounds. The 22,23 dihydro compounds and their preparation are described in European published patent application Ser. No. 8300435.1. This, of course, requires that the C-076 A1a/A1b and B1a/B1b pairs be separated from the A2a/A2b and B2a/B2b pairs of compounds, and then reduced to prepare the dihydro derivatives. The main problem encountered with this procedure is that the A2a/A2b and B2a/B2b compounds remain unused, and in effect wasted.

The process of the instant invention removes this waste by converting the unused compounds into the 22,23-unsaturated precursors of the biologically preferred compounds, or into the even more biologically preferred 22,23-dihydro derivatives.

SUMMARY OF THE INVENTION

The instant invention involves processes for the conversion of certain C-076 compound into other C-076 compounds and derivatives. In particular, this invention involves processes for the conversion of C-076 A2a/A2b into C-076 A1a/A1b or the 22,23 dihydro C-076 A1a/A1b; and the conversion of C-076 B2a/B2b into C-076 B1a/B1b or the 22,23 dihydro C-076 B1a/B1b. Thus, it is an object of this invention to describe the processes for the conversion of such C-076 compounds into the preferred C-076 compounds and derivatives. It is a further object of this invention to describe the protecting groups and reactions therefor which facilitate the foregoing reactions. Further processes will become apparent from reading the following description.

DESCRIPTION OF THE INVENTION

As mentioned above, the instant process achieves the conversion of the C-076 A2a/A2b and B2a/B2b into the preferred C-076 A1a/A1b and B1a/B1b compounds, and also the 22,23-dihydro derivatives thereof.

As is noted from the foregoing structure, the A2a/A2b and B2a/B2b compounds have a hydroxy group at the 23-position with the broken line indicating a single bond. The conversion of the C-076 A2a/A2b and B2a/B2b compounds into the A1a/A1b and B1a/B1b compounds thus involves the conversion of the 23-hydroxy group into 22,23 double bond. The conversion of the C-076 A2a/A2b and B2a/B2b compounds directly into the 22,23 dihydro C-076 A1a/A1b and B1a/B1b involves the removal of the 23-hydroxy and the retention of the 22,23-single bond.

The C-076 A2a/A2b compounds have, in addition to the 23-hydroxy group, a hydroxy group at the 4" position. The C-076 B2a/B2b compounds have additional hydroxy groups at the 5 and the 4" position. If this reaction is to be successfully carried out, the hydroxy group at the 5 and 4" positions must be protected, since it is an important feature of this process that only the 23-hydroxy group is permanently changed.

The preferred protecting group for the 4" and 5 positions is a trisubstituted silyloxy acetyl group. The most preferred group is the tert-butyldimethylsilyloxy acetyl group. The 4"-protected C-076 A2a/A2b and the 4",5-diprotected C-076 B2a/B2b compounds are prepared by combining the C-076 compound in an aprotic solvent such as methylene chloride, toluene, benzene, ethylacetate, tetrahydrofuran and the like and adding the protecting reagent which is the acid halide of the protecting group. The preferred reagent is tert-butyl-dimethylsilyloxy acetyl chloride. Also, in order to minimize side reactions, there is included in the reaction mixture a tertiary amine to react with the acid halide released during the course of the reaction. Preferred amines are pyridine and triethylamine. The tertiary amine is required in amounts equimolar to the amount of acid halide liberated, however, generally several multiples of the amine are employed. It is even possible to dispense with the solvent and use the amine in such excess that such amine, in effect becomes the solvent. The reaction is stirred at from 0° C. to the reflux temperature of the reaction mixture and is complete in from ½ to 16 hours.

Another protecting group is the trisubstituted silyl group, such as the alkyl substituted silyl group. The preferred group the tert-butyldimethylsilyl group. The hydroxy groups are protected by reactions with the trisubstituted silyl halide, preferably the chloride. The reaction conditions are similar to those employed for the preparation of the trisubstituted silyloxy acetyl substituent. This protecting group is removed by stirring in methanol with a catalytic amount of an acid, preferably a sulfonic acid such as p-toluene sulfonic acid. The reaction is complete in about 1–12 hours at from 0° to 50° C.

Other useful protecting groups are acyl and substituted acyl, particularly loweralkanoyl substituents such as acetyl, trifloroacetyl, trichloroacetyl, chloroacetyl, hydroxyacetyl, phenoxyacetyl, and the like. Such acylated compounds are prepared using such acylating reagents as the halide, preferably the chloride, of the acyl group being substituted on the substrate. Additional reagents such as the anhydride or haloformate are also useful.

In those reactions employing a halide reagent, it is advantageous to include in the reaction mixture a basic compound capable of reacting with and neutralizing the hydrogen halide liberated during the course of the reaction. Tertiary amines are preferred such as triethylamine, pyridine, dimethylamino pyridine, diisopropyl ethylamine, and the like. The basic compound is required in equimolar amounts relative to the moles of hydrogen halide liberated, however, excess amounts, even using the basic compound as a solvent, are not detrimental.

The starting materials are acylated in a solvent, preferably pyridine, at from 0° C. to room temperature, preferably room temperature, and are complete in from 4–24 hours. The products are isolated using known techniques.

The acyl protecting groups are readily removed by hydrolysis of the protected compound catalyzed with a mild base in a lower alkanol at from 0° C. to room temperature, and is complete in from 1–24 hours.

With the 4"- and 5-positions protected, the 23-hydroxy group is reacted with a substituted thiocarbonyl halide of the formula:

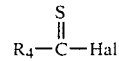

wherein Hal is a halogen such as fluorine, chlorine, bromine or iodine, although chlorine is preferred; and $R_4$ is substituted phenoxy wherein the substituent is loweralkyl; a di-substituted amino wherein the substituents are loweralkyl.

The reaction results in the substituted thiocarbonyloxy group at the 23-position. The reaction is carried out in an aprotic solvent such as those listed above for the protection of the 4"- and 5-positions. In addition, the presence of a tertiary amine is recommended and, as above, may be used in excess to the exclusion of any other solvent. The reaction is completed in about ½ to 16 hours at room temperature with most reactions being completed in about 7 hours. The thiocarbonyl halide reagent is generally used in excess, preferably having from a 1 to 10 molar excess of such reagent. The preferred reagent for use in this reaction is the (4-methyl phenoxy)thiocarbonyl chloride.

The 23-(substituted thiocarbonyloxy) compounds are the starting materials for the reaction for the preparation of the 1-series of compounds as well as for the dihydro compounds.

The C-076 A1a/A1b and B1a/B1b compounds are prepared according to the following reaction scheme showing the partial structural formulae of the protected intermediates:

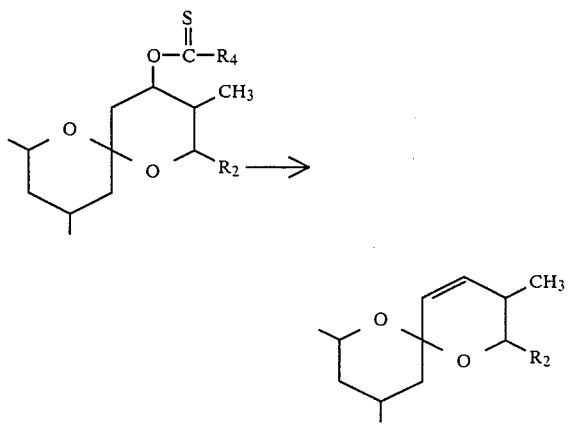

The reaction is a cis-elimination reaction of the thiocarbonyloxy leaving group and is carried out by heating the intermediate neat or in a high boiling solvent such as trichlorobenzene at about 150°–250° C. for from ½ to 3 hours. The products are isolated using techniques known to those skilled in the art. The products which are recovered are the 4",5-protected C-076 A1a/A1b and B1a/B1b compounds. The protecting groups are removed following the procedure described below.

The 23-substituted thiocarbonyloxy compound is used to directly prepare the 22,23-dihydro compound by reduction with tributyltin hydride in the presence of a free radical initiator. The reaction follows the course outlined below showing the partial structural formulae of the protected intermediates:

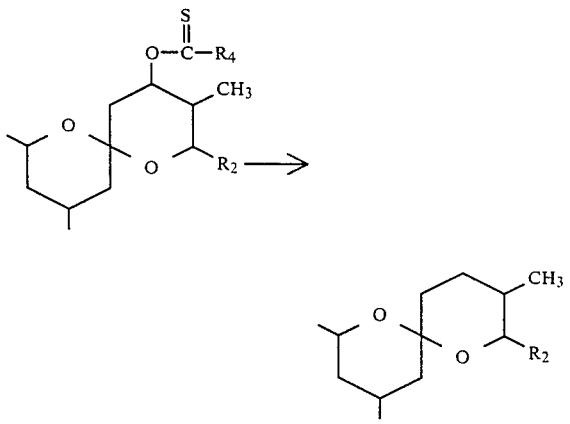

The reaction with the tributyltin hydride is carried out in an aprotic solvent such as toluene, at reflux or about 80°–110° C. and is complete in about 1–6 hours. The course of the reaction is monitored by techniques such as thin layer chromatography. If the reaction is seen to be incomplete, an additional amount of tributyltin hydride and free radical initiator is added, and the reaction heated for an additional 1–6 hours.

The preferred free radical initiator is azobisisobutyronitrile, which is employed in catalytic amounts. Other free radical initiators may be employed such as ultraviolet light or heat. If ultraviolet light is employed, the reaction temperature may be lowered, however, thin layer chromatographic analysis may reveal the need for additional reaction times. If heat is used as the free radical initiator, additional reaction may also be required. The product is isolated using known techniques.

The products recovered from the foregoing reactions having the trisubstituted silyloxy acetyl protecting group at the 4"- and 5-positions have such protecting groups removed in two steps. In the first step the protected compound is stirred at room temperature in a lower alkanol such as methanol, for about 30 minutes in the presence of p-toluene sulfonic acid. A single molar equivalent of p-toluene sulfonic acid is employed.

The product from this reaction has at the 4"- or 5-positions the hydroxy acetoxy group. That is, the tert-butyl trimethyl silyl group has been removed. Following this, the protected intermediate is treated with sodium methoxide in methanol at room temperature for from ½ to 2 hours. The hydroxy acetyl group is cleaved, leaving the hydroxy group, which product is isolated using techniques known to those skilled in this art.

Alternatively, the trisubstituted silyloxy acetyl protecting group may be removed in one step. Treatment with sodium methoxide at about room temperature for up to 6 hours will generally afford the desired unprotected product.

The compounds prepared by the processes of this invention, as well as the compounds from which they are prepared, are very active antiparasitic agents. They are, in particular, very useful as anthelmintics, ectoparasiticides, insecticides and acaricides, in human and animal health and in agriculture. When used in human and animal therapy, the compounds may be administered orally, in a solid or liquid formulation, as a unit dosage formulation or in the food or feed of the animal; or the compound may be administered as an injectable liquid solution of suspension. Dosages of from 0.025 to 0.5 mg. per kg. of animal body weight are effective. In agricultural uses, the compounds may be administered as a liquid spray or a solid dust to be applied to the plants or the soil in which they are growing; or they may be applied to the crops in bulk storage or as they are packaged or processed.

EXAMPLE 1

22,23-Dihydro C-076 B1a

A. 4",5-Di-O-(tert-butyl-dimethylsilyloxyacetyl) C-076 B2a

In a flame dried reaction vessel containing dry nitrogen are combined 2.0 gm. of C-076 B2a, 25 ml. of diethyl ether and 2.5 ml. of dry pyridine. The solution is cooled to 0° C. in an ice bath and 8 ml. of a diethyl ether solution containing 940 mg. of tert-butyl dimeythylsilyloxyacetyl chloride is added along with 600 mg. of tert-butyl dimethylsilyl chloride. The addition produces a white precipitate. The reaction mixture is stirred for 30 minutes in an ice bath after which thin layer chromatographic analysis indicates that the reaction is not yet complete. An additional 8 ml. of an ether solution containing 100 mg. of tert-butyl dimethylsilyloxyacetyl chloride per ml. of solution is added and the reaction mixture stirred for an additional 80 minutes. Thin layer chromatographic analysis indicated the absence fo starting material in the reaction mixture. 200 Ml. of cold water is added to the reaction mixture which is then extracted 5 times with 100 ml. portions of diethyl ether. The combined ether extracts are washed 7 times with 20 ml. portions of water and once with a 1:1 mixture of water and aqueous saturated sodium chloride. The ether layer is dried over mangesium sulfate and evaporated to dryness in vacuo. The residue is combined twice with diethyl ether, once with toluene and once again with diethyl ether and dried under high vacuum affording 3.2 g. of a clear white foam which is purified on a column of 175 g. of silica gel eluting with 15% ethylacetate and methylene chloride. The first 500 ml. of eluant is discarded and 20 ml. fractions are collected thereafter. Fractions 39–63 are collected affording 1.34 g. of a white foam which is indicated by mass spectrometry, and 300 mHz nuclear magnetic resonance to be 4″-5-di-O-(tert-butyl-dimethylsilyloxyacetyl) C-076 B2a.

B.
4″,5-di-O-(tert-butyl-dimethylsilyloxyacetyl)-23-O-([4-methylphenoxy] thiocarbonyl) C-076 B2a 570 Mg. of 4″,5-di-O-(tert-butyl dimethylsilyloxy acetyl C-076 B2a is combined with 5 ml. of pyridine and stirred under a blanket of nitrogen in an ice bath. 0.5 Ml. of O-(4-methylphenyl)chlorothioformate is added. An orange precipitate forms. The ice bath is removed and the reaction mixture is stirred for 5 hours. The reaction mixture darkens during this period. The reaction is poured into ice water and ether and saturated sodium chloride is added. The layers are separated and the aqueous layer twice more extracted with ether. The organic layers are combined and washed with water 5 times and once with saturated sodium chloride. The solution is dried over magnesium sulfate and evaporated to dryness, affording 1.59 g. of a dark brown oil. The oil is preliminary purified on 65 g. of silica gel eluting with 700 ml. of methylene chloride through a short column. Then a 30% ethylacetate in methylene chloride eluent is used affording 700 mg. of a brown foam which is placed on 7 preparative layer chromatography plate of 1500µ of silica gel eluting twice with 20% ethyl acetate in hexane. 242 Mg. of a beige foam is recovered which is identified by mass spectrometry and nuclear magnetic resonance as 4″,5-di-O-(tert-butyl-dimethylsilyloxyacetyl)-23-O-([4-methylphenoxy] thiocarbonyl) C-076 B2a.

C.
4″,5-Di-O-(tert-butyl-dimethylsilyloxyacetyl)-22,23-dihydro C-076 B1a

In a flame dried reaction vessel under dry nitrogen are combined 250 mg. of 4″,5-di-O-(tert-butyl dimethylsilyloxyacetyl)-23-O-[(4-methylphenoxy)]thiocarbonyl] C-076 B2a, 7 ml. of dry toluene and 25 mg. of azobisisobutyronitrile. The reaction mixture is heated in an oil bath to 120° C. whereupon 7 ml. of a toluene solution containing 0.5 ml. of tributyltinhydride is added in 0.5 ml. portions. The reaction mixture is stirred for 60 minutes and the toluene removed under a stream of nitrogen. The reaction mixture is dissolved in methylene chloride and placed on a column of 125 g. of silica gel and eluted with methylene chloride. 325 Ml. of eluant is discarded and the eluant changed to ethyl acetate. The first 200 ml. is discarded and then the column washed until the eluant shows no product. The eluant is dried and evaporated to dryness affording 310 mg. of 4″,5-di-O(tert-butyl-dimethylsilyloxyacetyl)-22,23-dihydro C-076 B1a which is used as is in the next reaction.

D. 4″,5-di-O-(hydroxyacetyl)-22,23-dihydro C-076 B1a

310 Ml. of 4″,5-di-O-(tert-butyl-dimethylsilyloxyacetyl)-22,23-dihydro C-076 B1a is combined in 60 ml. of a 1% p-toluene sulfonic acid solution of methanol and the reaction mixture stirred at room temperature for 30 minutes. The reaction is poured onto cold sodium bicarbonate solution and extracted 3 times with ether. The combined organic layers are washed 4 times with water, once with saturated sodium chloride solution, and dried over magnesium sulfate. The solution is concentrated to dryness in vacuo affording 250 mg. of solid material which is dissolved in methylene chloride and placed on two 2000µ preparative layer chromatography silica gel plates and eluted with 10% tetrahydrofuran 0.3% ethanol and methylene chloride. The slowest moving fraction contains 130 mg. of a white material which mass spectrometry and 300 mHz nuclear magnetic resonance indicate to be the product.

E. 22,23-Dihydro C-076 B1a

In a flame dried reaction vessel under dry nitrogen is combined 95 mg. 4″,5-di-O-(hydroxyacetyl) 22,23-dihydro C-076 B1a in a methanol solution of sodium methoxide prepared from 30 mg. of metallic sodium and 13 ml. of dry methanol, 10 ml. of methanol is applied to dissolve the starting material. The reaction mixture is stirred at room temperature for 30 minutes, poured onto a mixture of 100 ml. of diethyl ether and 50 ml. of water containing 0.4 ml. of acetic acid. The layers are separated and the aqueous layer extracted twice with diethyl ether. The combined ether layers are washed once with dilute sodium bicarbonate, 4 times with water and once with saturated sodium chloride solution. The organic layer is dried over magnesium sulfate and evaporated to dryness in vacuo affording 75 ml. of a yellow film. It is identified by 300 mHz nuclear magnetic resonance as 22,23-dihydro C-076 B1a, which compares favorably with an authentic sample. The residue is further purified by dissolving in methylene chloride and placed on a 1000µ silica gel preparative layer chromatography plate and eluted twice with 20% ethyl acetate in methylene chloride. 73 Mg. of a white foam is obtained which is purified again on another preparative layer chromatography plate and eluted with 20% tetrahydrofuran in chloroform affording 63 mg. of a clear glass material which is identified by 300 mHz nuclear magnetic resonance as 22,23-dihydro C-076 B1a.

EXAMPLE 2

C-076 B1a

A. 4″,5-Di-O-(tert-butyl dimethylsilyloxyacetyl) C-076 B1a

10 Mg. of 4″,5-di-O(tert-butyl dimethylsilyloxyacetyl)-23-O-[(4-methylphenoxy)thiocarbonyl] C-076 B2a as obtained in Example 1B is dissolved in 0.2 ml. of 1,2,4-trichlorobenzene and heated under a stream of nitrogen in an oil bath at 200° C. for 1 hour and 45 minutes. The reaction mixture is cooled to room temperature and diluted with methylene chloride and placed on a single 1000µ silica gel preparative layer chromatography plate and eluted with 30% ethylacetate in methylene chloride affording 8.5 mg. of a clear film which is dissolved in methylene chloride and placed on 250µ silica gel preparative layer chromatography plate and eluted twice with 2.5% tetrahydrofuran, and 0.1% ethanol in methylene chloride and once with 10% ethylacetate in methylene chloride. A slower moving band affords 4 mg. of a clear film which is identified by 300 mHz nuclear magnetic resonance and mass spectroscopy to be 4",5-di-O-(tert-butyl dimethylsilyloxyacetyl) C-076 B1a.

B. C-076 B1a/B1b

13 Mg. of 4",5-di-O-(tert-butyldimethylsilyloxyacetyl) C-076 B1a/B1b is dissolved in 1 ml. of dry methanol. 80 μL. of a previously prepared solution of sodium methoxide in methanol (from 28 mg. of sodium and 10 ml. of methanol) are added. The reaction is kept at 18° C. for 2½ hours and then added to a solution of 2 drops of acetic acid in 6 ml. of water. The product is extracted with ether, washed with water, dried and concentrated under a stream of nitrogen. Further purification by chromatography on a thin layer of silica gel gives 5 mg. of C-076 B1a/B1b. Using high pressure liquid chromatography and nuclear magnetic resonance spectroscopy, this material compares favorably with an authentic sample obtained by fermentation.

EXAMPLE 3

C-076 A1a

A. 4"-O-Acetyl-23-O[(4-methylphenoxy)thiocarbonyl] C-076 A2a

50 Mg. of C-076 A2a 4"-O-acetate is dissolved in 15 drops of dry pyridine and 3 drops of (4-methylphenyl)chlorothioformate is added at room temperature affording an immediate orange precipitate which redissolves after 10 minutes of stirring. The reaction mixture is stirred overnight at room temperature, combined with water and extracted 3 times with ether. The combined organic layers are washed 5 times with water, dried over magnesium sulfate and evaporated to dryness under a stream of nitrogen affording 100 mg. of a brown gummy material, which is dissolved in methylene chloride and placed on a 2000μ silica gel preparative layer chromatography plate and eluted with 5% tetrahydrofuran, 0.15% ethanol in methylene chloride affording 39.5 mg of an orange solid film, which mass spectroscopy indicates to be 4"-O-acetyl-23-O[(4-methylphenoxy)thiocarbonyl] C-076 A2a.

B. C-076 A1a 4"-O-acetate

10 Mg. of 23-O-[(4-methylphenoxy)thiocarbonyl] C-076 A2a 4"-O-acetate is heated at 200° C. for 20 minutes. The residue is dissolved in methylene chloride and placed on a 250μ silica gel preparative layer chromatography plate and eluted 5 times with 2.5% tetrahydrofuran 0.07% ethanol in methylene chloride. The slowest moving band is removed from the plate affording 1.7 mg. of a clear film which is identified by mass spectrometry and 300 mHz nuclear magnetic resonance as C-076 A1a 4"-O-acetate.

EXAMPLE 4

22,23-Dihydro C-076 A1a

A. 22,23-Dihydro C-076 A1a 4"-O-acetate 0.7 Ml. of dry toluene is combined with 0.1 ml. of tributyltinhydride and stirred while a solution of 5 mg. of 23-O(4-methylphenoxythiocarbonyl) C-076 A2a 4"-O-acetate in 0.3 ml. of dry toluene is added. The reaction mixture is stirred at reflux for 6 hours, the toluene removed under a stream of nitrogen while the reaction mixture is still warm and the residue diluted with methylene chloride which is placed on a single 500μ silica gel preparative layer chromatography plate and eluted with methylene chloride. The material at the origin of the plate is removed and dissolved in methylene chloride and placed on a 250μ silica gel preparative layer chromatography plate and eluted with 4% tetrahydrofuran and 0.1% ethanol in methylene chloride affording 22,23-dihydro C-076 A1a 4"-O-acetate, which is identified by mass spectrometry.

B. 22,23 Dihydro C-076 A1a

An aqueous methanolic sodium hydroxide solution is prepared from 0.065 ml. of 2.5-N aqueous sodium hydroxide, 0.5 ml. of methanol and diluted with water to a volume of 1.0 ml. 0.75 Ml. of this solution is added to a solution of 100 mg. of 4"-O-acetate-C-076-A1a in 2.5 ml. of methanol and stirred in an ice bath for 5 hours. The usual workup and purification on thin layer silica gel plates gives 30 mg. of C-076-A1a which is identical with an authentic sample obtained by fermentation.

EXAMPLE 5

22,23 Dihydro C-076 B1a

A. 23-O-[(4-Methylphenoxy)thiocarbonyl]C-076 B2a 4",5-di-O-acetate

20 Mg. of C-076 B2a 4",5-di-O-acetate is dissolved in 10 drops of dry pyridine and 2 drops of O-(4-methylphenyl)chlorothioformate is added affording a brownish precipitate which dissolves after stirring for 30 minutes at room temperature. The reaction mixture is stirred an additional 30 minutes and diluted with ice and water and extracted with ether 3 times. The combined organic layers are washed 5 times with water, dried over magnesium sulfate and evaporated under a stream of nitrogen affording 55 mg. of a brown solid, which is dissolved in methylene chloride and placed on a 2000μ preparative layer chromatography plate and eluted with methylene chloride containing 5% tetrahydrofuran and 0.15% ethanol. The slower moving spot affords 13.5 mg. of a light orange solid which is identified as 23-O-[(4-methylphenoxy)thiocarbonyl] C-076 B2a 4",5-di-O-acetate with 300 mHz nulcear magnetic resonance. The material is used as is in subsequent steps.

B. 22,23-Dihydro C-076 B1a 4",5-di-O-acetate

10 Mg. of 23-O-[(4-methylphenoxy)thiocarbonyl] C-076 B2a 4",5-di-O-acetate is dissolved in 0.4 ml. of dry toluene containing 5.2 mg. of tributyltin hydride and 0.15 mg. of azobisisobutyronitrile. The reaction mixture is refluxed for 2 hours whereupon thin layer chromatographic analysis indicates the reaction is not yet completed. An additional portion of 0.2 ml. of tributyltin hydride and 10 mg. azobisisobutyronitrile are added and the refluxing continued for an additional two hours. Thin layer chromatography indicates the reaction is still incomplete and an additional 0.2 ml. of tributyltin hydride and 10 mg. of azobisisobutyronitrile added and refluxing continued for 2 additional hours. Thin layer chromatography indicates the presence of product and the reaction mixture is evaporated under a stream of nitrogen and diluted with methlene chloride and placed on a column of 25 g. of silica gel in methylene chloride. The column is washed with 4 column volumes of methylene chloride to remove impurities and the eluant changed to ethyl acetate to collect the product in 4 column volumes. 10 Mg. of material is removed from the column and dissolved in methylene chloride and placed on a 250μ silica gel preparative layer chromatography plate and eluted twice with methylene chloride containing 4% tetrahydrofuran and 0.15% ethanol. The slower moving band is removed and identified with 300 mHz nuclear magnetic resonance and mass spectrometry as 22,23-dihydro C-076 B1a 4",5-di-O-acetate.

C. 22,23 Dihydro C-076 B1a

Deprotection of 22,23-dihydro C-076 B1a-4",5-di-O-acetate with aqueous-methanolic sodium hydroxide solution as described in Example 4B gives 22,23-dihydro C-076 B1a.

EXAMPLE 6

22,23-Dihydro C-076 B1a

A. 4",5-tert-butyl dimethylsilyl C-076 B2a

250 Mg. of C-076 B2a is dissolved in 2.5 ml. of dry dimethylformamide and combined with 115 mg. of imidazole and 130 mg. of tert-butyl dimethylsilyl chloride. The reaction mixture is stirred at room temperature for 10 hours, diluted with 50 ml. of ether and washed five times with water, dried over magnesium sulfate and evaporated to dryness in vacuo affording 380 mg. of residue. The residue is dissolved in methylene chloride and placed on three 1500μ silica gel prepartive layer chromatography plates and eluted with 7% tetrahydrofuran, and 0.2% ethanol in methylene chloride. The middle of the 3 major bands of product is isolated affording 127.7 mg. of a yellow syrup which is identified as 4",5-tert-butyldimethylsilyl C-076 B2a which is used as in subsequent steps.

B. 23-O([4-methylphenoxy]thiocarbonyl)-4",5-di-O-tert-butyl dimethylsilyl C-076 B2a 500 Mg. of 4",5-di-O-tert-butyl dimethylsilyl C-076 B2a is combined with 2.5 ml. of dry pyridine and stirred while 0.5 ml. of O-(4-methylphenyl)chlorothioformate is added dropwise. The reaction mixture is stirred at room temperature for 6 hours whereupon water and ether are added and the mixture shaken and the layers separated. The aqueous layer is extracted with ether and the combined organic layers are washed five times with water, dried over magnesium sulfate and evaporated to dryness in vacuo affording 1 g. of a dark brown gum. The residue is dissolved in methylene chloride and placed on five 2000μ silica gel preparative layer chromatography plates and eluted first with methylene chloride to remove impurities and then with 5% ethyl acetate in methylene chloride twice. The two fastest bands of material are separately chromatographed on four 1000μ silica gel preparative layer chromatography plates eluting with 4% ethyl acetate in methylene chloride. The fastest band on each of the two chromatograms are combined affording 210.5 mg. of a reddish brown foam which is identified by 300 mHz nuclear magnetic resonance and mass spectroscopy as 23-O[(4-methylphenoxy)thiocarbonyl]-4",5-di-O-tert-butyl dimethylsilyl C-076 B2a.

C. 4",5-Di-O-tert-butyl dimethylsilyl-22,23-dihydro C-076 B1a

50 Mg. of 4",5-di-O-tert-butyl dimethylsilyl 23-O-[(4-methylphenoxy)thiocarbonyl] C-076 B2a is combined with 0.1 ml. of tributyltin hydride, 5 mg. of azobisisobutylnitrile in 1.6 ml. of toluene and refluxed for 2 hours whereupon an additional 0.1 ml. of tributyltin hydride and 5 mg. of azobisisobutyronitrile is added and refluxing continued for 2 additional hours. The toluene is removed under a stream of nitrogen and diluted with methylene chloride and placed on a column of 25 g. of silica gel and eluted with methylene chloride to remove impurities. The solvent is changed to ethyl acetate, and the product is removed in 3 column volumes affording 50 mg. of a clear glass. The glass is dissolved in methylene chloride and placed on a 1000μ silica gel preparative layer chromatography plate and eluted with 4% ethyl acetate in methylene chloride followed by 6% ethyl acetate in methylene chloride. The fastest major band is removed affording 37.9 mg. of a yellow glass which mass spectrometry and 300 mHz nuclear magnetic resonance indicate as product.

D. 22,23-Dihydro C-076 B1a

A solution of 200 mg. of 4", 5-di-O-tert-butyldimethylsilyl-22,23-dihydro-C-076-B1a in 10 ml. of a 0.1% solution of p-toluene sulfonic acid hydrate in methanol is kept 14 hours at ambient temperature. Then it is diluted with ethylacetate, washed with aqueous sodium bicarbonate solution, water, dried and concentrated in vacuo to a liquid glass. This is further purified by chromatography a 1000μ silica gel plate to give 9 mg. of pure 22,23-dihydro C-076-B1a.

EXAMPLE 7

C-076 B1a

A. 4″,5-Di-O-tert-butyl dimethylsilyl C-076 B1a

50 Mg. of 4″,5-di-O-tert-butyl dimethylsilyl 23-O-[(4-methylphenoxy)thiocarbonyl] C-076 B2a as obtained in Example 6B is combined with 2.5 ml. of 1,2,4-trichlorobenzene and immersed in an oil bath at 200°–210° C. under a nitrogen atomsphere for 45 minutes. the reaction mixture is placed on a column of 30 g. of silica gel and eluted with 3 column volumes of methylene chloride and then with 5% ethyl acetate in methylene chloride followed by 10% ethyl acetate in methylene chloride. The last elution solvent mixture affords 60 mg. of a yellowish film which is dissolved in methylene chloride and placed on two 1000μ silica gel preparative layer chromatography plates and eluted twice with 5% ethyl acetate in methylene chloride affording 19.6 mg. of yellow glass which is identified by mass spectrometry and 300 mHz nuclear magnetic resonance as 4″,5-di-O-tert-butyl dimethylsilyl C-076 B1a.

B. C-076-B1a

4″,5-Di-O-tert-butyldimethylsilyl C-076-B1a is deprotected as described in Example 6D to give pure C-076-B1a.

EXAMPLE 8

4″,5-Di-O-phenoxyacetyl c-076 B2a/B2b

1 G. of C-076 B2a/B2b is dissolved in 10 ml. of methylene chloride which contains 0.25 ml. of pyridine. The solution is placed under nitrogen and cooled in an ice bath. With stirring, 10 ml. of methylene chloride containing 0.39 ml. of phenoxyacetylchloride is added, and the mixture stirred for 1 hour in an ice bath. The reaction mixture is poured onto 100 ml. of ice water and extracted 3 times with ether. The combined ether extracts are washed 3 times with water, once with saturated sodium chloride, dried over magnesium sulfate, and evaporated to dryness in vacuo. The residue is chromatographed on 80 g. of silica gel eluting with 12% ethylacetate in methylene chloride. Fractions 1–10 are discarded; fractions 11–20 afford 49 mg. of a pale yellow film; and fractions 25–72 afford 880 mg. of a white foam which is identified by 300 mHz nuclear magnetic resonance as 4″,5-di-O-phenoxyacetyl C-076 B2a/B2b.

EXAMPLE 9

C-076-B1a/B1b

A.
4″,5-Di-O-phenoxyacetyl-23-O-[(4methylphenoxy)thiocarbonyl] C-076-B2a/B2b

100 Mg. of 4″,5-di-O-phenoxyacetyl C-076-B1a/B2b is dissolved in 1.0 ml. of anhydrous pyridine and 0.2 ml. of (4-methylphenyl)chlorothioformate is added at 18° C. and stirred for 16 hours. The reaction mixture is worked up by addition of water and extraction of the product with ether. The ether extract is washed with water, dried over magnesium sulfate, and concentrated under a stream of nitrogen to a brown oil, which is further purified by preparative thin layer chromatography to give pure 4″,5-di-O-phenoxyacetyl-23-O-[(4-methylphenoxy)thiocarbonyl] C-076-B2a/B2b characterized by mass spectrometry and nuclear magnetic resonance spectroscopy.

B.
4″,5-Di-O-phenoxyacetyl-22,23-dihydro-C-076-B1a/B1b

4″,5-Di-O-phenoxyacetyl-23-O[(4-methylphenoxy)-thiocarbonyl) C-076 B2a/B2b is reduced with tributyltin hydride according to Example 1E affording 4″,5-di-O-phenoxyacetyl-22,23-dihydro-C-076-B1a/B1b.

C. 22,23-Dihydro-C-076-B1a/B1b

100 Mg. of 4″,5-di-O-phenoxyacetyl-22,23-dihydro-C-076 B1a/B1b is dissolved in 2 ml. of methanol. 2 Ml. of a methanol solution previously saturated with ammonia gas at 0° C. is added and the reaction mixture is stirred for 75 minutes at 18° C. The product is isolated by evaporation of the reaction mixture in vacuo at 20° C. dissolved in ether, washed with water dried over magnesium sulfate and concentrated in a stream of nitrogen. The crude product is further purified by thin layer chromatography and the purified product is compared by high pressure liquid chromatography and 300 mHz nuclear magnetic resonance spectrum with authentic material prepared by catalytic hydrogenation of C-076 B1a/B1b.

D. C-076 B1a/B1b

4″,5-Di-O-phenoxyacetyl-23-O-[(4-methylphenoxy)-thiocarbonyl] C-076 B2a/B2b is pyrolized as described in Example 2A. The crude 4″,5-di-O-phenoxyacetyl-C-076-B1a/B1b is deprotected and purified as described in the previous example to give essentially pure C-076-B1a/B1b.

APPENDIX I

Preparation 1

The contents of a lyophilized tube of *Streptomyces avermitilis* MA-4680 is transferred aseptically to a 250 ml. Erlenmeyer flask containing 3050 ml. of Medium 1. The inoculated flask is incubated for 3 days at 28° C. on a rotary shaking machine at a speed of 220 RPM in a 2 inch radius circular orbit. At the end of this time, a 250 ml. Erlenmeyer flask containing 50 ml. of Medium 2 is inoculated with a 2 ml. sample from the first flask. This flask is incubated for 3 days at 28° C. on a rotary shaking machine at a speed of 220 RPM in a 2 inch diameter circular orbit. 50 Ml. of the resulting fermentation broth containing C-076 is effective against an N.dubius infection in mice.

| Composition of Media | |
|---|---|
| Medium 1 | |
| Dextrose | 20 g. |
| Peptone | 5 g. |
| Meat Extract | 5 g. |
| Primary Yeast | 3 g. |
| NaCl | 5 g. |
| CaCO$_3$(after pH adjustment) | 3 g. |
| Distilled Water | 1000 ml. |
| pH 7.0 | |
| Medium 2 | |
| Tomato Paste | 20 g. |
| Modified Starch (CPC) | 20 g. |
| Primary Yeast | 10 g. |
| CoCl$_2$ 6H$_2$O | 0.005 g. |
| Distilled Water | 1000 ml. |
| pH 7.2–7.4 | |

Preparation 2

A lyophilized tube of *Streptomyces avermitilis* MA-4680 is opened aseptically and the contents suspended in 50 ml. of Medium 1 in a baffled 250 ml. Erlenmeyer flask. This flask is shaken for 3 days at 28° C. on a rotary shaking machine 220 RPM with a 2 inch diameter circular orbit. A 0.2 ml. portion of this seed medium is used to inoculate a Slant of Medium 3. The inoculated slant medium is incubated at 28° C. for 10 days and stored at 4° C. until used to inoculate 4 more slants of Medium 3. These slants are incubated in the dark for 8 days. One of these slants is used to inoculate 3 baffled 250 ml. Erlenmeyer flasks containing 50 ml. of No. 4 Seed Medium. The seed flasks are shaken for 2 days at 27° to 28° C. on a rotary shaking machine at 220 RPM with a 2 inch diameter circular orbit The contents of these flasks are pooled and used to inoculate (5% inoculum) baffled 250 ml. Erlenmeyer flasks containing 40 ml. of various production media. Flasks containing media 2, 5 and 6 are incubated for 4 days at 28° C. on a rotary shaking machine at 220 RPM with a 2 inch diameter circular orbit. The resulting broth containing C-076 is then harvested and tested for anthelmintic activity. In all cases 6.2 ml. of whole broth and the solids obtained from centrifuging 25 ml. of whole broth are fully active against N.dubius helminth infections in mice.

| Medium 3 (Slant Medium) | |
|---|---|
| Dextrose | 10.0 g. |
| Bacto Asparagine | 0.5 g. |
| K$_2$HPO$_4$ | 0.5 g. |
| Bacto Agar | 15.0 g. |
| Distilled Water | 1000 ml. |
| pH 7.0 | |
| Medium 4 (Seed Medium) | |
| Soluble Starch | 10.0 g. |
| Ardamine pH | 5.0 g. |
| NZ Amine E | 5.0 g. |
| Beef Extract | 3.0 g. |
| MgSO$_4$ 7H$_2$O | 0.5 g. |
| Cerelose | 1.0 g. |
| Na$_2$HPO$_4$ | 0.190 g. |
| KH$_2$PO$_4$ | 0.182 g. |
| CaCO$_3$ | 0.5 g. |
| Distilled Water | 1000 ml. |

-continued

| pH 7.0-7.2 | |
| --- | --- |
| Medium 5 | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |
| pH 6.8 | |
| Trace Element Mix | |
| $FeSO_4.7H_2O$ | 1000 mg. |
| $MnSO_4.4H_2O$ | 1000 mg. |
| $CuCl_2.2H_2O$ | 25.0 mg. |
| $CaCl_2$ | 100.0 mg. |
| $H_2BO_3$ | 56.0 mg. |
| $(NH_4)_2MoO_4.4H_2O$ | 10.0 mg. |
| $ZnSO_4.7H_2O$ | 200.0 mg. |
| Distilled Water | 1000 ml. |
| pH | |
| Medium 6 | |
| CPC Industrial Starch | 40.0 g. |
| Modified (Available from CPC Corp.) | |
| Distiller's Solubles | 7.0 g. |
| Autolyzed Yeast (Ardamine pH | 5.0 g. |
| available from Yeast Products Inc. | |
| $CoCl_2.6H_2O$ | 50.0 mg. |
| Distilled Water | 1000 ml. |
| pH 7.3 | |

Preparation 3

A 0.5×1.0 cm. loop of one of the four slants of Medium 3 prepared as in Example 2 is used to inoculate a baffled 250 ml. Erlenmeyer flask containing 50 ml. of Seed Medium No. 4. The seed flask is shaken for 1 day at 27° to 28° C. on a rotary shaking machine at 220 RPM with a 2 inch diameter circular orbit. The seed flask is then stored stationary at 4° C. until it is ready to be used. The contents of this flask are then used to inoculate (5% inoculum) 20 unbaffled 250 ml. Erlenmeyer flasks containing 40 ml. of Medium No. 2. After 4 days incubation at 28° C. on a rotary shaking machine at 220 RPM with a 2 inch diameter circular orbit, 19 of the flasks are harvested and pooled. The combined fermentation broths containing C-076 are filtered affording 500 ml. of filtrate and 84 g. of mycelia. 78 G. of mycelia are extracted with 150 ml. of acetone for ½ hour with stirring and the mixture filtered. The filter cake is washed with 50 ml. of acetone and the filtrate and washings are combined and concentrated to 46.5 ml. 30 Ml. of the concentrate is adjusted to pH 4 with dilute hydrochloric acid and extracted 3 times with 30 ml. portions of chloroform. The extracts are dried by filtering through dry Infusorial Earth (Super-Cel) combined and concentrated to dryness in vacuo. The oily residue of C-076 weighing 91.4 mg. is dissolved in chloroform sufficient to make 3 ml. of solution which represents 1% of broth volume. The C-076 obtained in this recovery procedure is fully active against N.dubius infections in mice. In addition, the chloroform extraction achieved a 70 fold purification of C-076 from the whole broth.

Preparation 4

A seed culture is prepared by inoculating 50 ml. of Medium 4 in a 250 ml. baffled Erlenmeyer flask with a 0.5×1.0 cm. loop from one of the four slants of Medium 3 as prepared in Example 2. The flask is incubated at 28° C. on a rotary shaking machine at 220 RPM with a 2 inch diameter circular orbit for 2 days. The seed culture is used to inoculate a 2 liter Erlenmeyer production flask containing 250 ml. of Medium 2. The inoculum volume is 5.0 ml. (2%). The production flask is incubated at 28° C. on a rotary shaker at 220 RPM for 4 days. At the end of this time the whole broth containing C-076 is harvested. 6 Ml. of this whole broth when tested in a mouse infected with N.dubius is found to be fully active.

Preparation 5

Step A

A 250 ml. baffled Erlenmeyer flask containing 50 ml. of Medium 7 is inoculated with a frozen vial of *Streptomyces avermitilis* MA-4680. The flask is incubated at 28° C. on a rotary shaking machine at 160 RPM with a 2 inch diameter circular orbit at 160 RPM for 24 hours.

| Medium 7 | |
| --- | --- |
| Dextrose | 1 gm. |
| CPC Industrial Starch Modified | 10 gm. |
| Meat Extract | 3 gm. |
| NZ Amine E | 5 gm. |
| Autolyzed Yeast (Ardamine pH) | 5 gm. |
| $MgSO_4.7H_2O$ | 0.05 gm. |
| $Na_4HPO_4$ | 0.19 gm. |
| $KH_2PO_4$ | 0.182 gm. |
| CaCO | 0.5 gm. |
| Distilled Water | 1000 ml. |
| pH 7.0-7.2 | |

Step B

Two 2 liter baffled Erlenmeyer flasks containing 500 ml. each of Medium 7 are inoculated with 10 ml. of the flask contents of Step A. The media are incubated at 28° C. on a rotary shaking machine at 160 RPM with a 2 inch diameter circular orbit for 24 hours.

Step C

To a 756 liter stainless steel fermentor containing 467 liters of Medium 8 is added 1 liter of the whole fermentation media from Step B. The fermentor is stirred at 28° C. at 130 RPM for 96 hours and with aeration at an air flow of 10 cubic feet per minute.

| Medium 8 | |
| --- | --- |
| Tomato Paste | 20 gm./l |
| Primary Yeast N.F. | 10 gm./l |
| Starch, modified, CPC | 20 gm./l |
| $CoCl_2.6H_2O$ | 5 mg./l |
| Polyglycol 2000 | 0.321 ml./l |
| Distilled Water | q.s. |
| pH 7.2-7.4 | |

At the end of this time 15.5 l. of the whole broth is filtered and the mycelia containing C-076 washed with water. The wet mycelia (2,268 g.) are extracted with 3 liters of acetone with stirring. The mixture is filtered and the filtrate concentrated to 1550 ml. and adjusted to pH 4.0 with dilute HCl. This solution is extracted 3 times with equal volumes of chloroform. The chloroform extracts are dried by filtering through dry Infusorial Earth (Super-Cel), combined and concentrated to dryness in vacuo. The residual oil of C-076 weighs 5.12 g. 3.3 Mg. is fully active against N.dubius in mice.

4.69 G. of this oil is dissolved in 142 ml. of chloroform and chromatographed on a column containing 90 g. of silica gel packed in chloroform. The column is developed with 1400 ml. of chloroform. The column is then eluted with chloroform/ethanol (49:1) collecting 145 cuts of 5 ml. each. Following this the column is eluted with chloroform/ethanol (19:1) collecting fractions 146–226 of 5 ml. each. Fractions 49–72 are combined and evaporated to dryness affording 200 mg. of an oil (A). Fractions 79–184 are likewise combined and evaporated affording 291 mg. of an oil (B). 400 µg of each fraction is fully active against N.dubius in mice. These two fractions (A and B) are analyzed separately on silica gel thin layer chromatographic plates (Quanta/Gram QIF plates, available from Quanta/Gram Inc., Fairfield, N.J.). The plates are developed with chloroform/methanol (19:1). The spots are analyzed for their ultraviolet activity and one spot of each fraction has the characteristic ultraviolet absorption for the C-076 compounds (see Table I). From fraction A, the spot with an Rf of 0.83 and from fraction B the spot with an Rf of 0.57 have such absorption. These spots represent the C-076 A compounds and the C-076 B compounds respectively.

198 Mg. of the oil (A) above is chromatographed on 80 g. of silica gel packed in chloroform, eluting with chloroform/methanol (199:1) until 520 ml. is collected, followed by chloroform/methanol (99:1) collecting fractions of 10 ml. each. The fraction from 630 to 720 ml. affords 30.4 mg.; the fraction from 730 to 950 ml. affords 78.4 mg. and the fraction from 950 to 1040 ml. affords 20 mg. of an oily material. Fractions 1 and 2 containing C-076 A components when tested in mice against N.dubius at levels of 1.0, 0.5 and 0.25 mg. are fully active.

Preparation 6

Step A

A 250 ml. baffled Erlenmeyer flask containing 50 ml. of Medium 8 is inoculated with a frozen vial of *Streptomyces avermitilis* MA 4680. The flask is incubated at 28° C. on a rotary shaking machine at 160 RPM with a 2 inch diameter circular orbit for 24 hours.

Step B

A 2 liter baffled Erlenmeyer flask containing 500 ml. of Medium 8 is inoculated with 10 ml. of the flask contents of Step A. The medium is incubated at 28° C. on a rotary shaking machine at 160 RPM with a 2 inch diameter circular orbit for 24 hours.

Step C

To a 189 liter stainless steel fermentor containing 160 liters of Medium 9 is added 500 ml. of inoculum from Step B. The fermentor is incubated at 28° C. with stirring at 150 RPM for 24 hours aerating at a rate of 3 cubic feet per minute.

| Medium 9 | |
| --- | --- |
| Dextrose | 1 gm./l |
| Corn Starch | 10 gm./l |
| Meat Extract | 3 gm./l |
| Autolyzed Yeast (Ardamine pH) | 5 gm./l |
| MgSO$_4$.7H$_2$O | 0.05 gm./l |
| Na$_2$HPO$_4$ | 0.10 gm./l |
| KH$_2$PO$_4$ | 0.182 g./l |
| CaCO$_3$ | 0.5 gm./l |
| Distilled Water | q.s. |
| pH 7.0–7.2 | |

Step D

To a 756 liter stainless steel fermentor containing 467 liters of Medium 6 is added 43 liters of inoculum from Step C. The fermentor is incubated at 28° C. with stirring at 130 RPM for 144 hours and with aeration at an air flow rate of 10 cubic feet per minute.

Step E

At the end of this time, the whole broth is filtered and the filter cake containing C-076 is washed with water. The filter cake is slurried in 120 liters of acetone for 30 minutes, filtered and the solids washed with 30 liters of acetone. The acetone washings are combined and evaporated under reduced pressure to a volume of 40 liters. The concentrate is adjusted to pH 4.0 with dilute hydrochloric acid. The concentrate is extracted 3 times with equal volumes of chloroform. The chloroform extracts are dried by filtering through a pad of dry Infusorial Earth (Super-Cel). The extracts are passed through the Super-Cel, then combined. The combined extracts are concentrated under reduced pressure to a volume of 4 liters. The chloroform concentrate is filtered and passed through a column of 2.4 kg. of silica gel in chloroform. The column is eluted with chloroform collecting eight 3.5 liter fractions. The column is then eluted with chloroform/methanol (49:1) collecting eight more 3.5 liter fractions (fractions 9–16). Fraction number 3 is concentrated to dryness affording 76 g. of an oily material containing a preponderance of the C-076 materials.

97% of this material is dissolved in 685 ml. of methylene chloride and chromatographed through 800 g. of silicic acid (Mallinckrodt Chemical Co. 100 mesh seived again through an 80 mesh screen). The column (7.62 cm. diameter, 36 cm. length) is developed with methylene chloride/benzene (7:3), about 7.5 l, followed by 5% isopropanol in methylene chloride/benzene (7:3), 2.25 l. The fraction eluted with the 5% isopropanol in methylene chloride/benzene, which contains a strongly colored band, contains virtually all of the C-076 material, as determined by thin layer chromatography (as described in Example 5). This fraction (500 ml.) is evaporated and rechromatographed on 105 g. of silicic acid (column 3.7 cm. diameter, 18 cm. length) in methylene chloride. The column is developed with 100 ml. portions of methylene chloride containing 5, 10 and 20% ether. Further elution with 20% ether in methylene chloride produces 2 colored bands. The fractions between the two bands contained virtually all of the C-076 material as determined by thin layer chromatography.

The C-076 containing fraction is chromatographed on 59 g. of silicic acid (column 3.7 cm. diameter, 11 cm. length) in methylene chloride. The column is developed with 10% ether in methylene chloride. After the first material begins to elute, a fraction of 70 ml. is taken followed by 26 fractions of 5–6 ml. each. Fractions 3–26 are combined, affording 1.35 g. of material, and analyzed by thin layer chromatography (silica gel plates-Analtech GF 254, developed with 5% isopropanol in methylene chloride). The material with an Rf of 0.28 in this system is C-076 A1.

The column is then eluted with 20% ether in methylene chloride (200 ml.) followed by 50% ether in methylene chloride (800 ml.). A small amount of C-076 A1/A2 mixture is eluted followed by all C-076 A2. The total residue of the C-076 A2 fraction is 800 mg.

Further elution with 5% isopropanol in methylene chloride affords C-076 B1 (135 mg.). The separation is followed by observing the ultraviolet absorption of the eluent. C-076 B1 and A2 have very similar Rf values on silica gel thin layer chromatography plates (Analtech GF 254) in 5% isopropanol in methylene chloride. However, the two components are clearly distinguishable on the same plates developed with 15% isopropanol in hexane.

The entire C-076 A1 fraction is applied to 14 silica gel plates (Analtech HF 254, 20×20 cm. 500μ thick). The plates are developed in 10% isopropanol in hexane. The band containing the C-076 A1 is removed from the plates, extracted with ether, evaporated and reapplied to 6 more plates and developed 5 times with 5% isopropanol in hexane. The C-076 A1 is removed from the plates and again chromatographed, developing with pure ether affording 270 mg. of substantially pure C-076 A1. The infrared and nuclear magnetic resonance spectra for this sample are reproduced as FIGS. 1 and 5 and Table II respectively.

The C-076 A2 fraction is chromatographed on 10 silica gel (Analtech HF 254) plates, developing 5 times with 15% isopropanol in hexane affording 265 mg. of substantially pure C-076 A2. The infrared and nuclear magnetic resonance spectra for this sample are reproduced in FIGS. 2 and 6 respectively, and Table II.

The C-076 B1 fraction is chromatographed on 2 plates (as above) in 15% isopropanol in hexane affording 55 mg. of substantially pure C-076 B1. The nuclear magnetic resonance spectrum of this sample is reproduced in FIG. 7, and Table II.

Preparation 7

The fermentation described in Example 6 is repeated twice and the whole broths are combined. The fermentation broth is worked up as described in Example 6 recovering 3.3 l of an initial chloroform extract which contains 60 mg./ml. of total solids and is estimated to be 0.5% C-076 by thin layer chromatographic analysis.

3 Liters of this chloroform solution is chromatographed on 2400 g. of silica gel (Davidson Grade 62) packed in chloroform. The column (9.5×122 cm.) is developed with eight 3800 ml. portions of chloroform (fractions 1–8) followed by eight 3800 ml. portions of chloroform/methanol (49:1 fractions 9–16). The individual fractions are analyzed by thin layer chromatography (silica gel plates, Quanta/Gram QIF) developed with chloroform/methanol 19:1. Fractions 9–11, 12–13 and 14 are each evaporated to dryness affording 6.63 g. of solids containing the C-076 A components in fractions 9–11, 24.91 g. of solids containing C-076 B components in fractions 12–13, and 4.71 g. of solids also containing the C-076 B components in fraction 14.

The material from fractions 12–14 are combined (29.62 g.), dissolved in 100 ml. of methylene chloride and chromatographed on 400 g. of silica gel (Davidson Grade 62) in methylene chloride. The column is eluted with 1500 ml. of methylene chloride/2-propanol (99:1); 1500 ml. of methylene chloride/2-propanol (49:1); 2000 ml. of methylene chloride/2-propanol (19:1); and 1000 ml. of methylene chloride/2-propanol (9:1). The eluent volumes between 5500–6000 ml. (2.56 g.) and 6000–6500 ml. (5.03 g.) are combined in 25 ml. of methylene chloride and chromatographed on 60 g. of silica gel in hexane. A forerun of 70 ml. of hexane and 100 ml. of hexane/diethyl ether (4:1) are taken and the column then developed with 600 ml. of hexane/diethyl ether (1:4) taking 200 ml. cuts, and finally eluting with 700 ml. of ether taking 100 ml. cuts. Column eluent volumes from 400 to 600 ml. affords 2.035 g. of solids containing C-076 B1 components; volumes 600–1100 contained 0.881 g. of solids containing mixed C-076 B1/B2 components; and volumes 1100–1500 ml. contained 0.381 g. of solids containing C-076 B2 components.

The mixed C-076 B1/B2 components are then dissolved in 4.2 ml. of methyl alcohol/water (4:1) and chromatographed on C18 Porasil (Bondapak-37–75 micron size) in the same solvent. The reverse phase high pressure column (more polar components eluted first) is 1.2 meters by 16 mm. and is eluted at a rate of 800 ml. per hour taking 21.3 ml. fractions. The presence of C-076 components is monitored by observing the ultraviolet absorption of the fractions. C-076 B2 is recovered in fractions 24 to 37 and C-076 B1 is recovered in fractions 51–70 recovering 195.4 mg. of C-076 B2 and 137 mg. of C-076 B1.

Each sample is then separately chromatographed on 4 g. columns of silica gel (Davidson Grade 62) in methylene chloride. The columns are eluted with 35 ml. of methylene chloride/methanol (9:1). The last 20 ml. of eluent from each column is collected and evaporated to dryness affording 155.3 mg. of C-076 B2 and 90 mg. of C-076 B1 respectively.

Then 50 mg. of C-076 B1 and 100 mg. of C-076 B2 are chromatographed on preparative silica gel plates (Analtech HF 254), developed with 12% isopropanol in hexane followed by development with ether, recovering C-076 B1 and C-076 B2 which are substantially pure. The infrared absorption spectrum of the thus recovered C-076 B1 and B2 is as shown in FIGS. 3 and 4 respectively. The nuclear magnetic spectrum of the thus recovered C-076 B2 is as shown in FIG. 8.

What is claimed is:

1. A process for converting C-076 A2a/A2b or C-076 B2a/B2b compounds into 22,23-dihydro C-076 B1a/B1b compounds respectively, which comprises reacting a C-076 A2a/A2b or C-076 B2a/B2b compound suitably protected at any hydroxy groups at the 4″ and 5 positions and unprotected at the 23 position hydroxy, with a substituted thiocarbonylhalide having the formula:

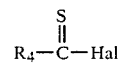

wherein Hal is a halogen selected from fluorine, chlorine, bromine or iodine, and $R_4$ is substituted phenoxy wherein the substituents are lower alkyl or disubstituted amino wherein the reaction is carried out at room temperature in an aprotic solvent and in the presence of a tertiary amine, to produce the 23-0 substituted thiocarbonyl compound, which is treated with tributyl tin hydride in an aprotic solvent in the presence of a free radical initiator selected from azobisisobutyronitrile, heat or ultraviolet light at from 80° to 110° C., to prepare the 22,23-dihydro compound; and said 22,23-dihydro C-076 A1a/A1b and 22,23-dihydro C-076 B1a/B1b compounds are prepared by removing any such protecting groups.

2. The process of claim 1 wherein Hal is chlorine.

3. The process of claim 1 wherein Hal is chlorine and $R_4$ is 4-methylphenoxy.

4. The process of claim 1 wherein the tertiary amine is triethylamine, pyridine, dimethyl amino pyridine, or diisopropylethylamine.

5. The process of claim 1 wherein the free radical initiator is azobisisobutyronitrile.

6. The process of claim 5 wherein the reaction with tributyltin hydride and azobisisobutyronitrile is carried out at from 80°–110° C.

* * * * *